(12) United States Patent
Kurata et al.

(10) Patent No.: US 6,723,430 B2
(45) Date of Patent: Apr. 20, 2004

(54) WATER-DECOMPOSABLE ABSORBENT ARTICLE

(75) Inventors: Nobuhiro Kurata, Kagawa (JP); Mitsuhiro Wada, Kagawa (JP); Sachiyo Suzuki, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 175 days.

(21) Appl. No.: 09/746,033

(22) Filed: Dec. 21, 2000

(65) Prior Publication Data

US 2001/0014566 A1 Aug. 16, 2001

(30) Foreign Application Priority Data

Jan. 6, 2000 (JP) ........................................ 2000-000577

(51) Int. Cl.⁷ .......................... D02G 3/00; B32B 27/00; A61F 13/20; A61F 13/15
(52) U.S. Cl. .................... 428/411.1; 428/378; 428/393; 428/394; 428/396; 604/385.01; 604/385.13; 604/358; 604/366; 604/367; 604/368; 604/369; 604/370; 604/371; 604/372
(58) Field of Search ........................ 604/385.01, 385.13, 604/358, 366–372; 428/378, 393, 394, 396

(56) References Cited

U.S. PATENT DOCUMENTS

| | | | | |
|---|---|---|---|---|
| 5,500,281 A | * | 3/1996 | Srinivasan et al. | 428/131 |
| 5,516,572 A | * | 5/1996 | Roe | 428/131 |
| 5,895,623 A | * | 4/1999 | Trokhan et al. | 264/504 |
| 6,068,620 A | * | 5/2000 | Chmielewski | 604/358 |
| 6,403,857 B1 | * | 6/2002 | Gross et al. | 604/365 |
| 2002/0065363 A1 | * | 5/2002 | Wang et al. | 525/58 |

FOREIGN PATENT DOCUMENTS

| | | | | |
|---|---|---|---|---|
| JP | 06-101154 | | 4/1994 | |
| JP | 08-019571 | | 1/1996 | |
| JP | 08-038547 | | 2/1996 | |
| WO | 97/185784 | * | 5/1997 | A61F/13/15 |
| WO | 00/59427 | | 10/2000 | A61F/13/15 |

OTHER PUBLICATIONS

Non-wovens Science and Technology—1999—Kermit Duckett.*
Derwent Abstract Accession No. 2000-551433/51, JP 3074478 B1 (Sakai KK) Aug. 7, 2000.

* cited by examiner

Primary Examiner—Terrel Morris
Assistant Examiner—Lynda Salvatore
(74) Attorney, Agent, or Firm—Darby & Darby

(57) ABSTRACT

Provided is a water-decomposable absorbent article including a water-decomposable back layer, a water-decomposable and liquid-pervious surface layer, and a water-decomposable absorbent layer sandwiched between the back layer and the surface layer. The absorbent layer is formed of at least one composite sheet of a water-soluble or water-swellable polymer layer and a water-decomposable fibrous layer, of which the uppermost layer adjacent to the surface layer is the water-decomposable fibrous layer.

6 Claims, 2 Drawing Sheets

WATER-DECOMPOSABLE ABSORBENT ARTICLE

BACKGROUND OF THE INVENTION

1. Field of the Invention

The present invention relates to a water-decomposable absorbent article for pantiliners, sanitary napkins, incontinence pads, diapers, and the like.

2. Description of the Related Art

Recently, absorbent articles disposable in flush toilets have come available, including, for example, pantiliners, sanitary napkins, incontinence pads, diapers, etc. For example, Japanese Unexamined Patent Publication (Kokai) Nos. Heisei 8-38547 and 8-19571 disclose water-decomposable absorbent articles comprising a water-decomposable absorbent layer and water-decomposable surface and back layers between which the absorbent layer is sandwiched.

As having such a water-decomposable back layer, these water-decomposable absorbent articles have a problem in that the excretions having been absorbed by the absorbent layer therein may lower the strength of the back layer that have received them, and may pass outside through the back layer.

To solve the problem, the water-decomposable back layer is covered with a water-insoluble (water-impervious) film to thereby prevent the liquid leakage through it; or a water-repellent sheet is used for the back layer. However, such a water-insoluble film or water-repellent sheet greatly lowers the decomposability in water of absorbent articles having it.

Japanese Unexamined Patent Publication (Kokai) No. Heisei 6-101154 discloses an absorbent article, in which the back layer of a water-decomposable material is covered with a water-soluble polymer film of polyvinyl alcohol (PVA) and an absorbent layer is provided on the polymer film. In the absorbent article disclosed in this publication, the PVA film is to prevent the leakage of excretions to the back layer. In this, however, the PVA film underlies the absorbent layer, and the PVA film and the absorbent layer are separated. Therefore, the excretions having passed through the absorbent layer will concentrate locally in the PVA film and will dissolve the local area of the PVA film in which they have concentrated. As a result, the PVA film will be locally holed or broken, and could not ensure satisfactory leakage prevention.

On the other hand, the absorbent layer may be thickened so that it can absorb the majority of excretions to thereby prevent the back layer from being kept in contact with a large amount of liquid. However, such a thick absorbent layer is unfavorable since the absorbent articles having it could not be soft and will have a hard feel.

SUMMARY OF THE INVENTION

An object of the invention is to provide a water-decomposable absorbent article which can surely prevent a liquid leakage through it, without having a hard feel, and can well decompose in water.

According to one aspect of the invention, a water-decomposable absorbent article may comprise a water-decomposable back layer, a water-decomposable and liquid-pervious surface layer, and a water-decomposable absorbent layer sandwiched between the back layer and the surface layer, wherein;

the absorbent layer is formed of at least one composite sheet of a water-soluble or water-swellable polymer layer and a water-decomposable fibrous layer, of which the uppermost layer adjacent to the surface layer is the water-decomposable fibrous layer.

For the absorbent layer of the absorbent article according to the invention, a fibrous layer is integrated with a water-soluble or water-swellable polymer layer to form a composite sheet. The excretions having been absorbed by the absorbent article reach the fibrous layer and diffuse therein, and then move to the polymer layer that is two-dimensionally integrated with the fibrous layer. Accordingly, in the absorbent article, the excretions do not locally concentrate in the water-soluble or water-swellable polymer layer. In this, therefore, the fibrous layer does not peel from the polymer layer, and the polymer layer is not holed or broken. As a result, the polymer layer that constitutes the absorbent layer surely acts to prevent the excretions from leaking out to the back layer. Since the polymer is soluble or swellable in water, the polymer layer easily decomposes in water when the absorbent article is disposed of in water.

The fibrous layer in the absorbent article of the invention may be made of tissue (water-decomposable paper), air-laid pulp, water-decomposable non-woven fabric or the like.

The absorbent layer in the absorbent article may be formed of two or more composite sheets stacked to each other, in each of which the water-decomposable fibrous layer is located to face the side of the surface layer.

The absorbent layer may be formed of one of the composite sheet which is folded into two so that constituent layers thereof are in an order of water-decomposable fibrous layer, polymer layer, polymer layer and water-decomposable fibrous layer with the uppermost water-decomposable fibrous layer being adjacent to the surface layer.

As set forth above, the embodiment of the absorbent article where the fibrous layers of tissue (water-decomposable paper) or the like are alternately laminated with the polymer layers is advantageous in that the excretions having been absorbed by it are more surely prevented from leaking out through the back layer. This is because, even when one of the polymer layers adjacent to the surface layer is decomposed by the excretions, the other fibrous layers and polymer layers underlying it can still ensure leakage prevention.

The water-soluble or water-swellable polymer layer may be, for example, a polyvinyl alcohol layer, and a basis weight (a basis weight is also referred to as Metsuke) of the polyvinyl alcohol layer is preferably at least 10 g/m². The polyvinyl alcohol layer may be in the form of a film, and it may be laminated and integrated with the fibrous layer. On the other hand, the polyvinyl alcohol layer may be formed on the fibrous layer by coating polyvinyl alcohol thereon, and this may be integrated with the fibrous layer.

If desired, an additional absorbent layer of pulp, tissue (water-decomposable paper) or the like may be provided between the composite sheet and the surface layer of the absorbent article of the invention.

According to another aspect of the invention, a water-decomposable absorbent article may comprise a water-decomposable back layer, a water-decomposable and liquid-pervious surface layer, and a water-decomposable absorbent layer sandwiched between the back layer and the surface layer, wherein;

the absorbent layer includes two water-decomposable fibrous layers and a water-soluble or water-swellable polymer layer sandwiched between the water-decomposable fibrous layers.

In this aspect of the invention, the absorbent layer comprises two fibrous layers of tissue, water-decomposable non-woven fabric, air-laid pulp or the like, and a polymer layer of PVA or the like sandwiched between the fibrous layers. The excretions having been absorbed by the absorbent article of this case first reach one fibrous layer adjacent to the surface layer, and then move to the polymer layer that underlies the fibrous layer. Therefore, they are prevented from penetrating into the back layer. In the absorbent article of this case, even when the polymer layer is dissolved by the excretions and the excretions thus having dissolved the polymer layer reach the other fibrous layer that underlies the polymer layer, they can be well absorbed by the underlying fibrous layer and are prevented from leaking out through the back layer.

The polymer layer in the absorbent article of this case may be formed on at least one fibrous layer by coating a polymer thereon; or a polymer film may be laminated on at least one fibrous layer to form the polymer layer thereon. As the case may be, a polymer film of PVA or the like may be simply sandwiched between two fibrous layer, without being bonded thereto.

DESCRIPTION OF THE PREFERRED EMBODIMENTS

Figure 1:
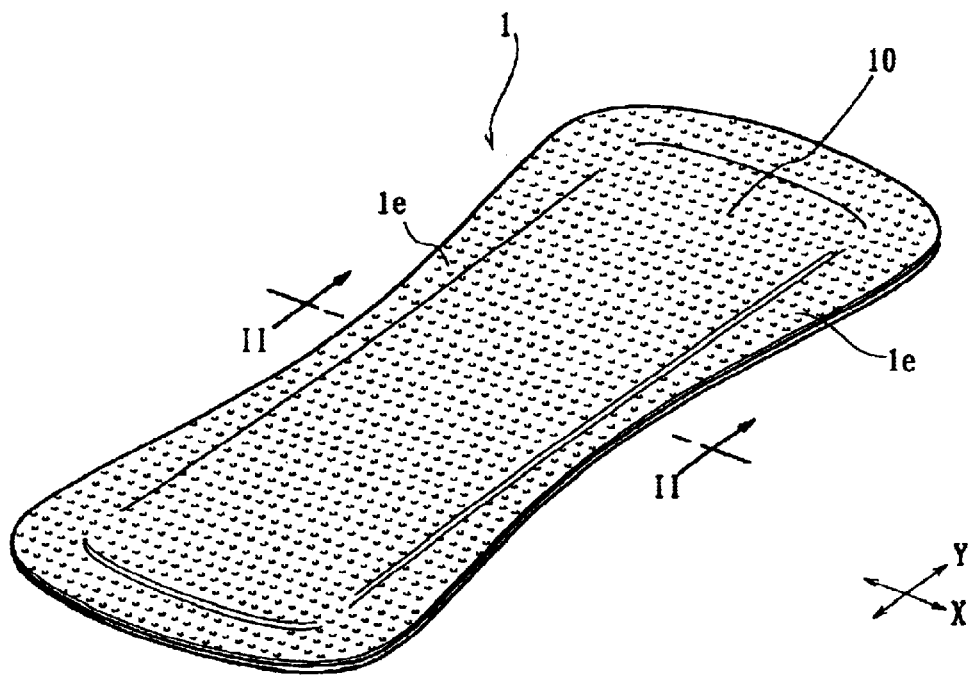
FIG. 1 is a perspective view of one embodiment of an absorbent article according to the invention.
Figure 2:
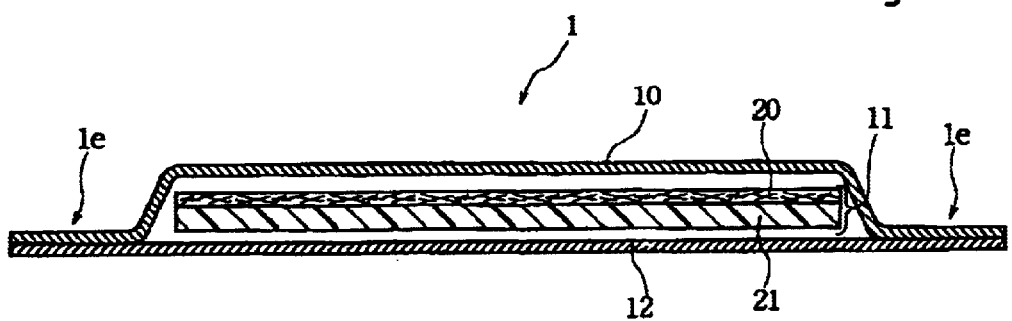
FIG. 2 is a cross-sectional view of the absorbent article of FIG. 1, cut along the line II—II.

The invention will be described with reference to the accompanying drawings. FIG. 1 is a perspective view of one embodiment of an absorbent article according to the invention, looking from a top surface thereof (this top surface serves as a body facing surface); and FIG. 2 is a cross-sectional view of the absorbent article of FIG. 1, cut along the line II—II. In these, the longitudinal direction of the absorbent article illustrated is designated by Y, and the transverse direction generally perpendicular to the direction Y is designated by X.

The absorbent article of the invention shown in FIG. 1 is for pantiliners or sanitary napkins, and this is decomposable in water. As shown in FIG. 2, the absorbent article 1 comprises a water-decomposable and liquid-pervious surface layer 10 that shall serve as the body facing surface, a water-decomposable back layer 12, and a water-decomposable absorbent layer 11 sandwiched between the surface layer 10 and the back layer 12. In an outer peripheral region 1e of the absorbent article 1 in which the absorbent layer 11 does not exist, the outer layer 10 and the back layer 12 are bonded to each other. In this region, the two layers are bonded to each other with a water-decomposable adhesive, or are heat-sealed with a water-decomposable thermoplastic adhesive, or are bonded via hydrogen bonding therebetween.

The surface layer 10 is, for example, made of a water-decomposable non-woven fabric of spun lace. On the other hand, a plurality of sheets of water-decomposable papers may be laminated on a water-decomposable non-woven fabric to form the surface layer 10. In this case, the non-woven fabric and the water-decomposable paper sheets may be integrated through hydrogen bonding or needling. Since the surface layer 10 acts to lead excretions to the underlying absorbent layer 11, it is preferably perforated to have a plurality of perforations throughout the entire area thereof, for example, as shown in FIG. 1. The perforations may be formed by needling.

The back layer 12 is readily dispersed in water jets in flush toilets or in water in septic tanks, and it may be formed of water-decomposable paper, water-decomposable non-woven fabric or the like that contains water-dispersible fibers. For example, it may be made of (1) a water-decomposable paper sheet of pulp fibers where the pulp fibers are bonded to each other via hydrogen bonding therebetween, (2) a water-decomposable paper sheet of pulp fibers and other water-dispersible fibers of rayon or the like where the constituent fibers are bonded to each other with a water-soluble binder, (3) a water-decomposable paper sheet of water-dispersible fibers where the constituent fibers are simply entangled, or (4) a water-decomposable non-woven fabric of water-dispersible fibers having a relatively short length where the constituent fibers are forcedly entangled through water-jetting treatment. Preferably, the outer surface of the back layer 12 (this outer surface serves as a garment facing surface) is coated with a water-soluble resin such as a polyvinyl alcohol, an unsaturated carboxylic acid copolymer or the like. Thus coated, the back layer 12 will be impervious to fluid.

The absorbent layer 11 may be made of a composite sheet in which a water-soluble or water-swellable polymer layer (gel layer) 21 of, for example, polyvinyl alcohol (PVA) is coated on an outer surface of a fibrous layer 20 of, for example, tissue (water-decomposable paper), water-decomposable non-woven fabric or air-laid pulp. On the other hand, the absorbent layer 11 may be made of a composite sheet (a laminate sheet) in which a polymer film of PVA or the like to be used as a polymer layer 21 is laminated on and integrated with the above-mentioned fibrous layer 20.

In the embodiment of FIG. 2, a fibrous layer 20 and a polymer layer 21 are integrated to form a composite sheet., and this one composite sheet forms the absorbent layer 11. In this case, the fibrous layer 20 overlies the polymer layer 21., and is adjacent to the surface layer 10. In the embodiment of FIG. 2, the polymer layer 21 is sandwiched between the fibrous layer 20 and the back layer 12. The constitution of the absorbent article of this embodiment differs from the conventional absorbent articles disclosed in Japanese Unexamined Patent Publication (Kokai) No. Heisei 6-101154 and the like, in that the polymer layer 21 is bonded to and integrated with the fibrous layer 20 in the former. Therefore, in the absorbent article of this embodiment, the excretions having passed through the surface layer 10 reach the absorbent layer 11, in which they are first absorbed by the fibrous layer 20 and diffuse therein, and thereafter the thus-diffused excretions move to the polymer layer 21. The excretions having been thus absorbed by the absorbent layer 11 do not locally concentrate in a limited area but widely diffuse in the fibrous layer 20, and then move to the polymer layer 21. Therefore, while the absorbent article is used, the polymer layer 21 is hardly holed or broken, and it does not easily peel off from the fibrous layer 20. As a result, the polymer layer 21 can effectively prevent a liquid leakage to the back layer 12. Furthermore, since the polymer layer 21 is soluble or swellable in water, it is readily decomposed in water when the used absorbent article is disposed of in toilets. In order that the excretions having diffused through the fibrous layer 20 can be surely kept in the polymer layer 21, it is desirable that a basis weight (a basis weight is also referred to as Metsuke) of the polymer layer 21 is at least 10 g/m².

The fibers for forming the fibrous layer 20 may be those of at least one sort selected from the group consisting of natural fibers and chemical fibers. The natural fibers include those from wood pulp such as soft wood pulp, hard wood pulp, etc.; and also those from Manila hemp, linter pulp, etc. These natural fibers are biodegradable. Among those, preferred are bleached soft-wood kraft pulp, and bleached hard-wood kraft pulp, as being highly dispersible in water. Also usable for the fibrous layer 20 are synthetic fibers, regenerated fibers of rayon or the like, biodegradable synthetic fibers, and synthetic pulp of polyethylene, etc. Among those, preferred is rayon, as being biodegradable. Any other fibers except for those set forth above are also usable, so far as they are dispersible in water.

The fibrous layer 20 may be made of a water-decomposable sheet (absorbent sheet) prepared through a paper-making process of such fibers, a water-decomposable non-woven fabric prepared by specifically processing the fibers through water-jetting treatment, or a fibrous web (e.g., air-laid pulp web) of the fibers. For example, a sheet of air-laid pulp having a basis weight (Metsuke) of from 50 to 70 g/m² or so may be formed into the fibrous layer 20. In the fibrous layer 20, the fibers may be bonded to each other with a water-soluble binder such as carboxymethyl cellulose or alkyl cellulose.

The polymer layer 21 may be coated on the outer surface of the fibrous layer 20. On the other hand, a polymer film to be used as the polymer layer 21 may be laminated on the outer surface of the fibrous layer 20. The polymer includes, for example, cellulose derivatives such as methyl cellulose, hydroxyethyl cellulose, carboxymethyl cellulose, etc.; water-soluble polymers such as polyvinyl alcohol, sodium alginate, sodium polyacrylate, polyacrylic ether, polyvinyl pyrrolidone, isobutylene-maleic anhydride copolymer, etc.; and also starch, dextrin, etc. Among those, preferred is polyvinyl alcohol; and more preferred are cold water-soluble PVA derivatives.

In case where a polyvinyl alcohol film is laminated on the fibrous layer 20, the polyvinyl alcohol film having a Metsuke of from 10 to 30 g/m², preferably from 15 to 25 g/m² or so may be subjected to heat sealing or thermal pressure sealing with being stacked on the fibrous layer 20. As the case may be, the polymer film for forming the polymer layer 21 may be two-dimensionally bonded to the fibrous layer 20 with a water-soluble adhesive or the like.

Figure 3:
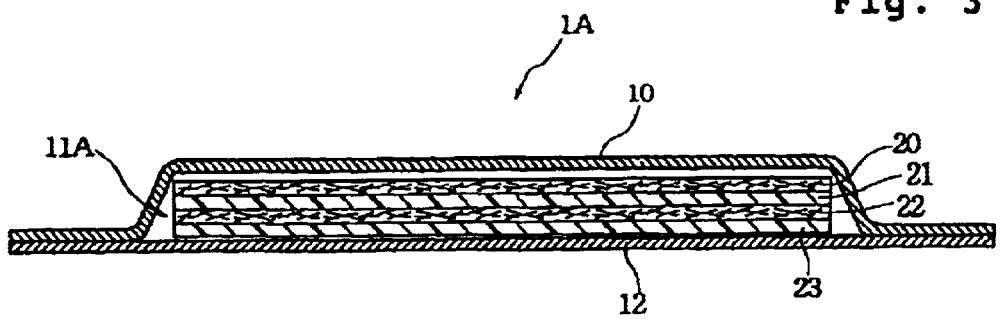
FIG. 3 is a cross-sectional view of another embodiment of the absorbent article according to the invention.
Figure 4:
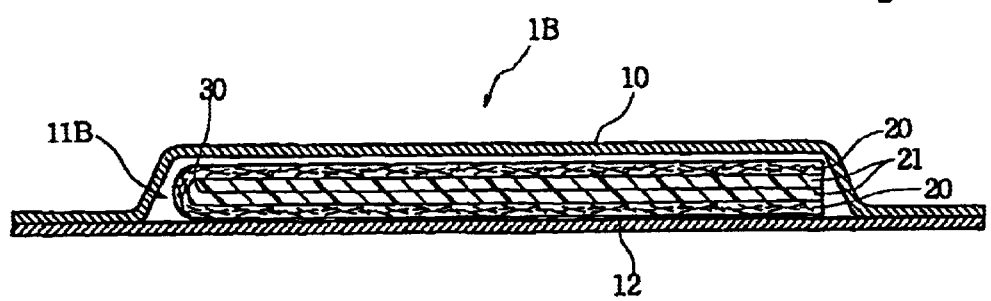
FIG. 4 is a cross-sectional view of still another embodiment of the absorbent article according to the invention.

FIG. 3 and FIG. 4 are cross-sectional views of other embodiments of the absorbent article according to the invention. Absorbent articles 1A and 1B of FIG. 3 and FIG. 4 differ from the absorbent article 1 of FIG. 2 in point of the structure of the absorbent layer therein.

In the absorbent article 1A of FIG. 3, the absorbent layer 11A is formed of two composite sheets. For this, each composite sheet comprises a water-soluble or water-swellable polymer layer and a water-decomposable fibrous layer, and the two layers are stacked (coated or laminated) and integrated. Briefly, the fibrous layer is coated with a polymer or is laminated with a polymer film to form the integrated composite sheet. In the absorbent article 1A, the constituent layers are disposed in the illustrated order of a water-decomposable fibrous layer 20, a polymer layer 21, a water-decomposable fibrous layer 22 and a polymer layer 23, with the fibrous layer 20 being adjacent to the surface layer 10.

With such a construction, the excretions having passed through the surface layer 10 of the absorbent article 1A of first reach the fibrous layer 20 and then the polymer layer 21. Even when the polymer layer 21 is dissolved by the excretions having passed through the fibrous layer 20, the excretions thus having passed through the polymer layer 21 can be further diffused in the underlying fibrous layer 22, and the thus-diffused excretions reach the still underlying polymer layer 23. The excretions thus having reached the polymer layer 23 are prevented from leaking out through the back layer 12. Accordingly, it can be expected that the absorbent article 1A is more effective for preventing a liquid leakage therethrough than the absorbent article 1 of FIG. 2.

In the embodiment of FIG. 3, the two composite sheets each comprising the integrated fibrous layer and polymer layer may be bonded to each other, that is, the polymer layer 21 may be bonded to the fibrous layer 22. In this case, the absorbent layer 11A is of a four-layered laminate sheet. As the case may be, the two composite sheets constituting the absorbent layer 11A may be bonded only in the vicinity of the outer periphery portions thereof to ensure the self-retention of the absorbent layer 11A.

The absorbent article 1B of FIG. 4 differs from the absorbent article 1 of FIG. 2 and the absorbent article 1A of FIG. 3 in point of the structure of the absorbent layer therein. In the absorbent article 1B, the absorbent layer 11B is formed of one composite sheet that comprises integrated fibrous layer 20 and polymer layer 21. For this, the polymer layer 21 is stacked (coated or laminated) on the fibrous layer 20 as is the case with the absorbent article 1A of FIG. 3. The composite sheet is folded into two along a folding line 30 extending in the direction Y of the absorbent article to form the absorbent layer 11B. Therefore, in the absorbent article 1B, the constituent layers are positioned in the illustrated order of a water-decomposable fibrous layer 20, a polymer layer 21, a polymer layer 21 and a water-decomposable fibrous layer 20, with the first fibrous layer 20 being adjacent to the surface layer 10 (the respective constituent layers are also referred to as an upper fibrous layer 20, an upper polymer layer 21, a lower polymer layer 21, and a lower fibrous layer 20, hereinafter).

The excretions having passed through the surface layer 10 of the absorbent article 1B of the illustrated case are first absorbed by the upper fibrous layer 20 and diffuse therein, and then move to the under lying polymer layer 21. Since the polymer layer 21 is folded to be two layers, i.e., the upper and lower polymer layers, the effect of preventing the excretions from leaking out of them to reach the back layer 12 is high. For example, even when the upper fibrous layer 20 has peeled off from the upper polymer layer 21 owing to the excretions having passed through the upper fibrous layer 20 and thereby the upper polymer layer 21 has been broken, the lower polymer layer 21 is still effective for preventing the leakage of the excretions through the absorbent layer 11B. Even when the excretions have passed through two upper and lower polymer layers 21, 21, the lower fibrous layer 20 can well absorb the excretions, thereby preventing them from leaking out through the back layer 12.

In the embodiments of FIG. 3 and FIG. 4 in which the absorbent layers 11A, 11B are respectively constituted so that the polymer layer is sandwiched between two fibrous layers, it is not always necessary that the polymer layer is integrated with the fibrous layers. As the case may be, for example, a water-soluble or water-swellable polymer film of PVA or the like may be simply sandwiched between the fibrous layers, without being bonded thereto. Still another embodiment of the absorbent layer applicable to the absorbent article of the invention is a three-layered absorbent layer that comprises a fibrous layer, a polymer layer and a fibrous layer in that order with either one of the fibrous layers being adjacent to the surface layer 10.

In the constitution of the absorbent layer which comprises a polymer film serving as a polymer layer to be sandwiched between two fibrous layers without being bonded to the fibrous layers, the excretions having passed through the upper fibrous layer are blocked by the interlayer of the polymer layer, and are therefore prevented from leaking out through the absorbent layer. In this, even when the polymer layer is broken by the excretions, the underlying fibrous layer can still absorb the excretions having passed through the polymer layer.

Figure 5:
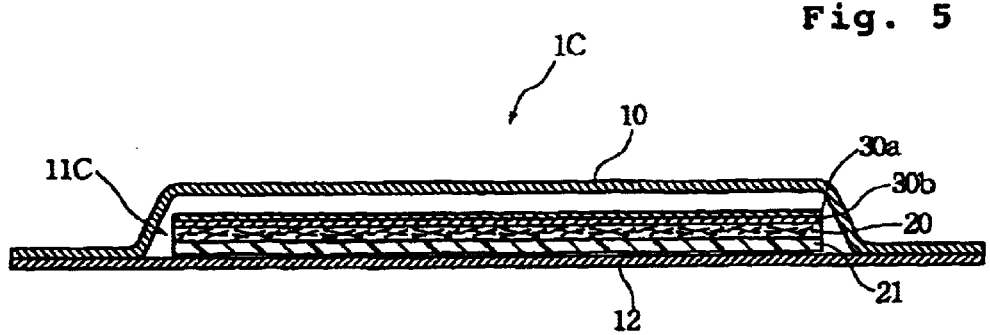
FIG. 5 is a cross-sectional view of still another embodiment of the absorbent article according to the invention.

FIG. 5 is a cross-sectional view of still another embodiment of the absorbent article of the invention. An absorbent article 1C of FIG. 5 differs from the absorbent article 1 of FIG. 2 in point of the structure of the absorbent layer therein. In the absorbent article 1C, the absorbent layer 11C is of a composite sheet that comprises a fibrous layer 20 laminated with a polymer layer 21. In this, layers of water-decomposable tissue 30a, 30b are further laminated on the composite sheet, and they are adjacent to the surface layer 10. In the absorbent article 1C of this case, the excretions having passed through the surface layer 10 are first absorbed by the water-decomposable tissue layers 30a, 30b and diffuse therein, and are thereafter absorbed by the fibrous layer 20 and diffuse therein. In this, therefore, a large amount of the excretions having been thus absorbed by the absorbent layer 11C do not locally concentrate in a limited area of the polymer layer 21 but move widely in the polymer layer 21. Accordingly, the leakage preventing effect of the polymer layer 21 is not lowered.

In the water-decomposable absorbent article of the invention, any other absorbent material may be provided between the sheet of the absorbent layer that comprises a fibrous layer laminated with a polymer layer, and the surface layer, as set forth above. In this case, the additional absorbent layer may be any of water-decomposable tissue paper, fibrous web of pulp or the like, or water-decomposable non-woven fabric.

Also in the embodiments of FIG. 3 and FIG. 4, such an additional absorbent layer of tissue or the like may be provided on the uppermost fibrous layer.

In the invention, it is desirable that the back side of the absorbent article, i.e., the outer surface of the back layer 12 (this outer surface serves as a garment facing surface) is entirely coated with an adhesive and covered with a release film which is to protect the capability of the adhesive while the absorbent article is not used. Also preferably, the release film is decomposable in water. Still preferably, the package to envelop the absorbent article is also decomposable in water.

EXAMPLES

The invention is described in more detail with reference to the following Examples, which, however, are not intended to restrict the scope of the invention.

For the examples of the invention, pantiliners were prepared as shown in FIG. 2, FIG. 3 and FIG. 4. These had a length of 140 mm and a width of 55 mm.

Example 1 is to demonstrate the absorbent article of FIG. 2; Example 2 is to demonstrate that of FIG. 3; and Example 3 is to demonstrate that of FIG. 4. For these, the surface layer 10 was made of a non-woven fabric of wet-spun lace, having a basis weight of 45 g/m$^2$; the back layer 12 was made of a non-woven fabric of wet-spun lace, having a basis weight of 45 g/m$^2$. To form the absorbent layer in these, an air-laid pulp sheet having a basis weight of 60 g/m$^2$ was used for the fibrous layers 20, 22; and a polyvinyl alcohol film having a basis weight of 20 g/m$^2$ was used for the polymer layers 21, 23.

In Comparative Example 1, the absorbent layer was made of only a fibrous layer of air-laid pulp having a basis weight of 60 g/m$^2$; and in Comparative Example 2, the absorbent layer was made of only a polyvinyl alcohol film having a basis weight of 20 g/m$^2$.

The pantiliners thus produced in the Examples and the Comparative Examples were subjected to a wear test, a test in a septic tank, and a test for decomposition in water. The data obtained are given in Table 1 below.

(Wear Test)

The samples were tested by ten panelists. After used, the condition of each sample was macroscopically checked. In Table 1, "◯" indicates that the tested samples were not broken; and "×" indicates that the tested samples were broken.

(Test in Septic Tank)

The samples were disposed of in a flush toilet and led to a septic tank. In the septic tank, the behavior of each sample was macroscopically checked. In Table 1, "◯" indicates that the samples were pulverized into individual layers immediately when led into the septic tank; and "×" indicates that the samples were not separated into individual layers.

(Test for Decomposition in Water)

The samples were tested according to the water-decomposability test in JIS P-4501. Precisely, each sample was cut to have a length of 10 cm and a width of 10 cm, put into a 300 ml beaker filled with 300 ml of ion-exchanged water, and stirred therein with a stirrer. The revolution of the stirrer was 600 rpm. While stirred, the sample was periodically checked, and the time taken by it until its dispersion in water was recorded. In Table 1, "◯" indicates that the samples were decomposed in water within 100 seconds; and "×" indicates that the samples were not decomposed in water.

TABLE 1

|  | Example 1 | Example 2 | Example 3 | Comparative Example 1 | Comparative Example 2 |
| --- | --- | --- | --- | --- | --- |
| Surface Layer | wet-spun lace | wet-spun lace | wet-spun lace | wet-spun lace | wet-spun lace |
| Absorbent Layer | one sheet of fibrous layer + PVA layer | two sheets of fibrous layer + PVA layer | one folded sheet of fibrous layer + PVA layer | fibrous layer only | PVA layer only |
| Bacl Layer | wet-spun lace | wet-spun lace | wet-spun lace | wet-spun lace | wet-spun lace |
| Wear Test | ◯ | ◯ | ◯ | × | × |
| Test in Septic Tank | ◯ | ◯ | ◯ | ◯ | ◯ |
| Test for Decomposition in Water | ◯ | ◯ | ◯ | ◯ | ◯ |

As set forth above in detail, the water-decomposable absorbent article of the invention effectively prevents liquid from leaking out through its back layer. For this, the absorbent layer is specifically constituted to comprise a polymer layer integrated with a fibrous layer, without increasing the basis weight of the absorbent layer. Therefore, the absorbent article has a good feel. When disposed of in flush toilets, the used absorbent article can be easily and surely decomposed in water.

While the invention has been described in detail and with reference to specific embodiments thereof, it will be apparent to one skilled in the art that various changes and modifications can be made therein without departing from the spirit and scope thereof.

Here, 'comprises/comprising' when used in this specification is taken to specify the presence of stated features, integers, steps or components but does not preclude the presence or addition of one or more other features, integers, steps, components or groups thereof.

What is claimed is:

1. A water-decomposable absorbent article comprising:
    a water-decomposable back layer,
    a water-decomposable and liquid-pervious spun-laced surface layer having a plurality of perforations on an entire area thereof, and
    a water-decomposable absorbent layer sandwiched between the back layer and the surface layer,
    wherein the absorbent layer is formed of composite sheet of a water-soluble or water-swellable polymer layer and a water-decomposable fibrous layer, the composite sheet being folded into two so that constituent layers thereof are arranged in an order of water-decomposable fibrous layer, polymer layer, polymer layer and water-decomposable fibrous layer with the uppermost water-decomposable fibrous layer being adjacent to the surface layer.

2. The water-decomposable absorbent article as set forth in claim 1, wherein the water-soluble or water-swellable polymer layer is polyvinyl alcohol layer.

3. The water-decomposable absorbent article as set forth in claim 2, wherein the polyvinyl alcohol layer has a basis weight of at least 10 $g/m_2$.

4. The water-decomposable absorbent article as set forth in claim 2, wherein the polyvinyl alcohol layer is in the form of a film which is laminated and integrated with the fibrous layer.

5. A water-decomposable absorbent article comprising a water-decomposable back layer, a water-decomposable and liquid-pervious spun-laced surface layer having a plurality of perforations on an entire area thereof, and a water-decomposable absorbent layer sandwiched between the back layer and the surface layer, wherein;
    the absorbent layer includes two water-decomposable fibrous layers and a water-soluble or water-swellable polymer layer sandwiched between the two water-decomposable fibrous layers.

6. The water-decomposable absorbent article as set forth in claim 5, wherein the water-soluble or water-swellable polymer layer is a film of polyvinyl alcohol.

* * * * *